United States Patent
Bagabas et al.

(10) Patent No.: US 8,362,302 B2
(45) Date of Patent: *Jan. 29, 2013

(54) COMPOSITE CATALYST AND USING THE SAME FOR MAKING ISOPROPYL ALCOHOL

(75) Inventors: Abdulaziz A Bagabas, Riyadh (SA); Mohamed Mokhtar Mohamed Mostafa, Cairo (EG); Abdulrahman A Al-Rabiah, Riyadh (SA); Vagif Malik Akhmedov, Baku (AZ)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 13/447,615

(22) Filed: Apr. 16, 2012

(65) Prior Publication Data

US 2012/0203034 A1      Aug. 9, 2012

Related U.S. Application Data

(63) Continuation-in-part of application No. 13/295,193, filed on Nov. 14, 2011, now abandoned.

(51) Int. Cl.
*C07C 45/72* (2006.01)
*C07C 27/00* (2006.01)
*B01J 23/06* (2006.01)
*B01J 23/60* (2006.01)

(52) U.S. Cl. ........ 568/388; 568/878; 502/307; 502/329; 502/343

(58) Field of Classification Search .................. 568/388, 568/878; 502/307, 329, 343
See application file for complete search history.

(56) References Cited

U.S. PATENT DOCUMENTS 5,495,055 A      2/1996   Rueter

*Primary Examiner* — Sikarl Witherspoon
(74) *Attorney, Agent, or Firm* — Geeta Kadambi Riddhi IP LLC

(57) ABSTRACT

Isopropyl alcohol is a very useful chemical that is widely used in the industry as a solvent. Economical and easy process to make ispopropyl alcohol using novel composite catalyst is described in the instant application. Production of isopropyl alcohol (IPA) from dimehtyl ketone (DMK) and hydrogen ($H_2$) in gas-phase using a ruthenium nano-particle-supported on activated charcoal/nano-zinc oxide composite catalyst is described. Gas phase production of isopropyl alcohol using DMK and hydrogen is also described using optimal time on stream, temperature, catalyst ratio and DMK/$H_2$ ratio. Ruthenium nano-zinc oxide composite catalyst is formulated using different ratios of ruthenium activated charcoal and n-ZnO is described. CAT-IV is shown to be the best performer for the efficient production of isopropyl alcohol.

13 Claims, 3 Drawing Sheets

COMPOSITE CATALYST AND USING THE SAME FOR MAKING ISOPROPYL ALCOHOL

CROSS REFERENCE TO RELATED APPLICATIONS

The instant application is a continuation-in-part and claims priority to pending U.S. application Ser. No. 13/295,193, filed on Nov. 14, 2011. The pending U.S. application Ser. No. 13/295,193 is hereby incorporated by reference in its entirety for all of its teachings.

FIELD OF THE INVENTION

The instant application relates to the production of isopropyl alcohol (IPA) from dimehtyl ketone (DMK) and hydrogen ($H_2$) in gas-phase using ruthenium nanoparticle-supported on activated charcoal/nano-zinc oxide composite catalyst.

BACKGROUND

The conversion of low-cost commodity chemicals such as DMK to high-value chemicals such as branched monoalchols, diols, α,β-unsaturated aldehydes, and α,β-unsaturated ketones is important for the industry. IPA is used as a solvent and for manufacturing different chemicals such as isopropyl amines and ethers. IPA has also other applications in medicine and industry. Several catalysts have been used for hydrogenation of DMK in the liquid-phase to produce IPA. An activated supported ruthenium catalyst was tested for the production of IPA via direct hydrogenation of aqueous DMK stream in the liquid phase (U.S. Pat. No. 5,495,055). A process and catalyst, which is capable of producing IPA by controlling the reaction conditions to make it economical, would be desirable for industry.

SUMMARY OF THE INVENTION

The invention discloses a novel composite catalyst and using the composite catalyst for the process of making the IPA in gas-phase from DMK and hydrogen. In one embodiment, process of making IPA using DMK and hydrogen with ruthenium nano-particle supported on activated charcoal with nano zinc oxide (n-ZnO) is disclosed. In another embodiment, catalyst in different ratios for optimizing the production and selectivity of IPA are disclosed.

In one embodiment, mechanical mixing of the commercially-available ruthenium nano-particle supported on activated charcoal with zinc oxide nano-particle (n-ZnO) for making the composite catalyst is disclosed. In another embodiment, thermal pyrolysis is performed to produce Zinc oxide nanoparticle (n-ZnO). In one embodiment, specific catalyst such as CAT-I, CAT-II, CAT-III, CAT-IV AND CAT-V were made and tested in the process of making IPA. The specific catalyst CAT-IV had the best results.

In one embodiment, the synthesis and using of five types of composite catalysts, made by the mechanical mixing of ruthenium nanoparticle supported on activated charcoal with zinc oxide nanoparticle in different ratios are disclosed. The ratio is 0-100 by weight percent for Ru/AC and Ru/AC:n-ZnO (wt/wt) is between 0:1 to 3:2 and 1:0.

The process of making IPA comprises of many conditions. Each condition has its own advantages and disadvantages. The optimum conditions are depicted in the present disclosure to produce the best output of IPA. The variable conditions are temperature, molar ratio of $H_2$/DMK, ratio of the composite component and time on stream.

In one embodiment, the optimal temperature for a reaction between DMK, hydrogen and the composite catalyst is between 75-375° C., more preferably for certain catalyst composite from 75-200° C. In another embodiment, the $H_2$/DMK mol ratio is between 1.5 to 6.

In one embodiment, the process of making the IPA involves making the composite catalyst at a certain ratio to optimize the hydrogenation sites on the catalyst for maximum selectivity of IPA.

The novel composite catalyst composition, method of synthesizing the novel catalyst and method of utilizing the novel catalyst in chemical reactions disclosed herein may be implemented in any means for achieving various aspects. Other features will be apparent from the accompanying figures and from the detailed description that follows.

BRIEF DESCRIPTION OF DRAWINGS

Example embodiments are illustrated by way of example and no limitation in the tables and in the accompanying figures, like references indicate similar elements and in which.

Figure 1:
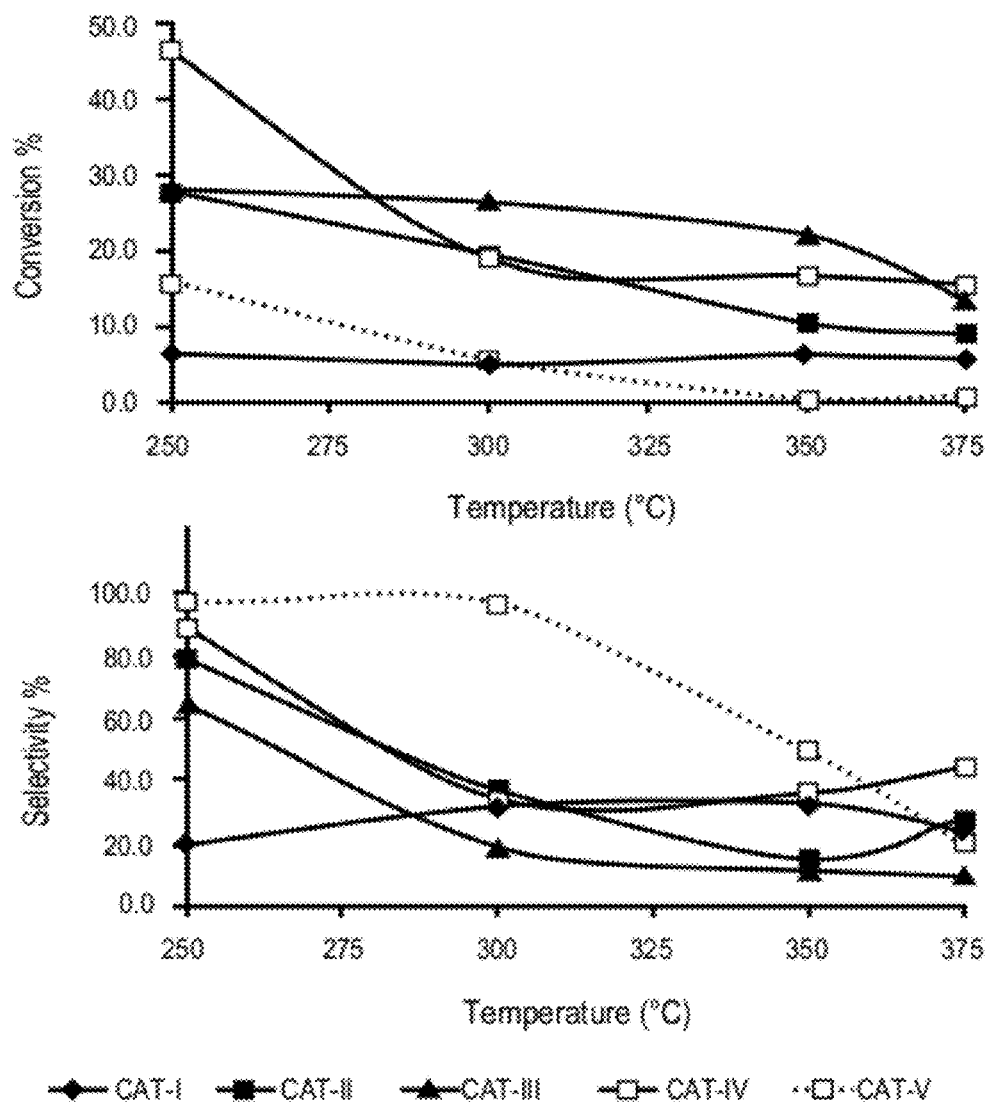
FIG. 1 shows DMK conversion and IPA selectivity over all tested catalysts at different temperatures ($H_2$/DMK mol ratio=6, Time on stream (TOS)=1 hr).

Other features of the present embodiments will be apparent from the accompanying figures, tables and from the detailed description that follows.

DETAILED DESCRIPTION

Several methods of synthesizing a novel ruthenium nanoparticle supported on activated charcoal with nano zinc oxide (n-ZnO) as a composite catalyst and utilizing the novel composite catalyst to increase the production of IPA and other by products are disclosed. Although the present embodiments have been described with reference to specific example embodiments, it will be evident that various modifications and changes may be made to these embodiments without departing from the broader spirit and scope of the various embodiments.

The present composite catalysts comprises of ruthenium nano-particle supported on activated charcoal mixed mechanically with zinc-oxide nano-particle. Ruthenium catalysts are less expensive and can be used for DMK hydrogenation. In addition, the activated charcoal support is superior when compared to other support materials because activated charcoal resists the formation of cock inside the reactor. Zinc oxide nano-particle may be partially reduced to zinc metal, which increases the IPA selectivity in the products.

The composite catalyst is used for synthesizing IPA by varying the reaction conditions. The catalytic reaction was carried out in the gas-phase. The novel composite catalysts may be used in liquid phase as well, but preferentially in gas-phase wherein the reaction could be carried out at atmospheric pressure. The catalytic performance of the said composite catalysts may be modified by varying the weight ratio of their components, by changing the hydrogen to DMK mole ratio, time on stream, and/or by changing the temperature.

Catalyst Preparation

Zinc pyruvic acid oxime complex was prepared from reacting zinc sulphate, sodium pyruvate, hydroxyl amine hydrochloride, and sodium bicarbonate. Thermal pyrolysis of zinc pyrovic acid oxime complex was done to produce zinc oxide nanoparticle (n-ZnO). This lab-made n-ZnO was mechanically mixed and ground with the commercially-available ruthenium-supported on activated charcoal (Ru/AC) at different weight ratios. A solid-solid wetting (mechanical mixing) method was adopted to synthesize the composite of Ru/AC/n-ZnO catalysts. Ru/AC and n-ZnO in different ratios were mixed thoroughly using a pestle and mortar then the mixture was pulverized and subsequently calcined at 400° C. for 12 h. The ratios of Ru/AC:n-ZnO used were as follows: 1:2 wt % (CAT-II), 1:1 wt % (CAT-III) and 3:2 wt % (CAT-IV). For comparison the pure n-ZnO (CAT-I) and pure Ru/AC (CAT-V) were also studied. The nominal compositions of the synthesized catalysts are given in Table 1.

TABLE 1

Chemical composition of the prepared catalysts:

| Catalyst | Ru/AC (wt %) | Ru/AC:n-ZnO (wt/wt) |
|---|---|---|
| CAT-I | 0 | 0:1 |
| CAT-II | 33.33 | 1:2 |
| CAT-III | 50 | 1:1 |
| CAT-IV | 60 | 3:2 |
| CAT-V | 100 | 1:0 |

Production of IPA Using Optimal Reaction Conditions and Composite Catalyst

The effect of temperature on the catalytic performance of the mentioned composite catalysts was investigated in the range between 100° C. and 375° C. at fixed $H_2$/DMK mole ratio of 4 or 6. Table 2 shows the variation of DMK conversion % and product selectivity % over the composite catalyst at fixed $H_2$/DMK mol ratio of 6, time-on-stream (TOS=1 hour), at 250° C., 300° C., 350° C., and 375° C. As shown in examples, decreasing temperature led to increase in DMK conversion and IPA selectivity. The highest DMK conversion (46.4%) was observed over CAT-IV at 250° C. CAT-IV also showed 87.6% selectivity towards IPA and 10.5% selectivity towards MIBK. However, the highest selectivity towards IPA (95.8%), concomitant with very low selectivity towards MIBK (1%), was observed over CAT-V at 250° C. CAT-V also showed a 15% DMK conversion rate. In contrast, the highest selectivity towards MIBK (69.3%), associated with low selectivity towards IPA (10%), was observed over CAT-III at 375° C. and 13.6% DMK conversion. These observations clearly indicate that addition and condensation reactions are favored over acidic/basic sites with elevating temperature while the direct hydrogenation reaction of DMK is favored with reducing temperature. Moreover, the catalyst identity plays a key role in DMK conversion % and in directing the reaction towards MIBK or IPA. CAT-I and CAT-V gave the lowest DMK conversion % and the lowest selectivity towards MIBK. This can be attributed to the catalyst lack of multi-functionality (balanced acidity/basicity and hydrogenation sites) required for synchronous addition, condensation, and hydrogenation reactions to overcome the reaction thermodynamic equilibrium limitation. For this reason, MO has the highest selectivity among all products at low DMK conversion % over CAT-I, which is acidic. The low selectivity towards IPA over this catalyst could be attributed to the partial reduction of zinc oxide to zinc metal. On the other hand, IPA had the highest selectivity among all products over CAT-V, owing to the predominance of hydrogenation sites on this catalyst.

TABLE 2

Gas-phase DMK-self condensation over n-Ru/AC/n-ZnO catalysts*

| Catalyst | Temp., ° C. | Conv., % | Selectivity, % | | | | | | |
|---|---|---|---|---|---|---|---|---|---|
| | | | MIBK | DIBK | MO | M | IPA | DA | Others |
| CAT-I | 250 | 6.7 | 0.9 | 0.1 | 59.4 | 0.0 | 19.9 | 0.0 | 19.7 |
| | 300 | 5.2 | trace | 0.0 | 48.9 | 0.0 | 31.6 | 0.0 | 19.5 |
| | 350 | 6.3 | trace | 0.0 | 48.7 | 0.0 | 32.2 | 0.0 | 19.1 |
| | 375 | 5.9 | 0.1 | 0.0 | 51.7 | 0.0 | 23.7 | 0.0 | 24.5 |
| CAT-II | 250 | 27.8 | 17.4 | 2.1 | 2.4 | 0.2 | 77.6 | 0.1 | 0.2 |
| | 300 | 19.4 | 50.6 | 7.8 | 2.2 | 1.2 | 36.3 | 0.5 | 1.4 |
| | 350 | 10.6 | 54.7 | 1.9 | 2.2 | 1.8 | 14.9 | 0.3 | 24.2 |
| | 375 | 9.1 | 53.5 | 2.5 | 5.2 | 0.5 | 27.2 | 1.0 | 10.1 |
| CAT-III | 250 | 28.2 | 25.8 | 4.0 | 2.9 | 0.7 | 64.4 | 0.2 | 2.0 |
| | 300 | 26.5 | 53.4 | 15.2 | 2.6 | 0.3 | 18.6 | 0.2 | 9.7 |
| | 350 | 22.0 | 62.8 | 14.3 | 1.6 | 0.4 | 11.2 | trace | 9.7 |
| | 375 | 13.6 | 69.3 | trace | 3.1 | trace | 10.0 | 0.1 | 17.5 |
| CAT-IV | 250 | 46.4 | 10.5 | 0.3 | 1.5 | 0.0 | 87.6 | 0.0 | 0.1 |
| | 300 | 19.1 | 50.8 | 8.0 | 2.0 | 0.8 | 34.2 | 0.0 | 4.2 |
| | 350 | 16.8 | 48.2 | 5.3 | 1.6 | 0.6 | 35.9 | 0.0 | 8.4 |
| | 375 | 15.5 | 46.2 | 5.0 | 1.4 | 0.6 | 44.0 | 0.1 | 2.7 |
| CAT-V | 250 | 15.6 | 1.0 | trace | trace | trace | 95.8 | 0.0 | 3.2 |
| | 300 | 5.7 | 0.4 | 0.0 | 0.6 | 0.0 | 94.9 | 0.0 | 4.1 |
| | 350 | 0.6 | 6.7 | 0.0 | 10.7 | 0.0 | 48.5 | 0.0 | 34.1 |
| | 375 | 0.9 | 3.0 | 0.0 | 8.6 | 0.0 | 19.5 | 0.0 | 68.9 |

*Reaction conditions: 0.25 g catalyst, $H_2$/DMK mol ratio = 6, time-on-stream = 1 hour.

Table 3 displays the variation of DMK conversion and product selectivity % over the composite catalysts at fixed H$_2$/DMK mol ratio of 4, time-on-stream (TOS=1 hour), at 250° C., 300° C., 350° C., and 375° C. The impact of temperature under these conditions on the DMK conversion %, IPA selectivity %, and MIBK selectivity % is similar to that observed under the conditions of Table 2. The reduction of H$_2$/DMK mol ratio from 6 to 4, however, explicitly has strong influence. It has led to a significant decrease of the highest DMK conversion from 46.4% at H$_2$/DMK mol ratio of 6 to 35.0% at H$_2$/DMK mol ratio of 4 over CAT-IV at 250° C. Such an observation might indicate the importance of hydrogen not only as a reactant but also as an activating agent for the composite catalyst. The highest selectivity towards MIBK (70.5%), associated with low selectivity towards IPA (9.6%) was observed over CAT-III at 350° C. and 19.3% DMK conversion. The highest selectivity towards IPA (95.6%), on contrast, coupled with negligible selectivity towards MIBK (0.4%), was observed over CAT-V at 300° C. and 5% DMK conversion. This low DMK conversion can be attributed to the increase in temperature, which has a negative influence on conversion upon increasing, as shown clearly from the data of Table 3. The lowest conversion of DMK was also observed over CAT-I and CAT-V due to the lack of multifunctionality, reflecting the importance of catalyst identity.

Table 4 shows the effect of temperature on the DMK conversion % and the selectivity % towards product at H$_2$/DMK mol ratio of 6, TOS of 1 hour, over CAT-IV. Reduction of temperature from 200° C. to 100° C. led to tremendous increases in DMK conversion from 56% to ~82% and IPA selectivity from 89% to ~100%. On the other hand, a huge reduction in the selectivity towards MIBK from 6% to 0% and MO from ~3% to ~0% was observed. These results confirmed the preference of the direct reduction of DMK to IPA over the self-condensation of DMK with reducing temperature. Moreover, these results are in parallel with the exothermic nature of reducing DMK to IPA.

TABLE 4

Gas-phase DMK-self condensation over n-Ru/AC/n-ZnO catalysts*

| Catalyst | Temp., ° C. | Conv., % | Selectivity, % | | | | | | |
|---|---|---|---|---|---|---|---|---|---|
| | | | MIBK | DIBK | MO | M | IPA | DA | Others |
| CAT-IV | 200 | 56.1 | 6.6 | trace | 2.7 | 0.0 | 89.2 | 0.0 | 1.5 |
| | 150 | 74.3 | 1.6 | trace | 0.8 | 0.0 | 96.3 | trace | 1.3 |
| | 100 | 81.8 | 0.0 | trace | trace | trace | 99.7 | trace | 0.3 |

Reaction conditions: 0.25 g catalyst, H$_2$/acetone mol ratio = 6, time-on-stream = 1 hour.

Table 5 shows that reduction of temperature to 75° C. has a strong impact on the DMK conversion and selectivity towards product depending on the H$_2$/DMK mol ratio. The highest conversion of DMK was achieved when the H$_2$/DMK mol ratio was 1.5. A reduction by ~2.7% in DMK conversion was observed upon increasing H$_2$/DMK mol ratio to 6. This reduction in DMK conversion could be attributed to the reduction in contact time when increasing the H$_2$/DMK mol ratio, which increased due to the increase in hydrogen flow rate. However, the selectivity towards IPA increases slightly from 98.7 to 99.8% upon increasing the H$_2$/DMK mol ratio from 1.5 to 6.0. This excellent IPA selectivity is due to the

TABLE 3

Gas-phase DMK-self condensation over n-Ru/AC/n-ZnO catalysts*

| Catalyst | Temp., ° C. | Conv., % | Selectivity, % | | | | | | |
|---|---|---|---|---|---|---|---|---|---|
| | | | MIBK | DIBK | MO | M | IPA | DA | Others |
| CAT-I | 250 | 1.5 | 0.3 | 0.0 | 65.1 | 0.0 | 14.9 | 0.0 | 19.7 |
| | 300 | 5.1 | trace | 0.0 | 55.1 | 0.0 | 26.4 | 0.0 | 18.5 |
| | 350 | 4.9 | trace | 0.0 | 50.9 | 0.0 | 32.8 | 0.0 | 16.3 |
| | 375 | 5.8 | 0.1 | 0.0 | 55.2 | 0.0 | 21.3 | 0.0 | 23.4 |
| CAT-II | 250 | 26.5 | 22.6 | 1.8 | 2.5 | 0.2 | 72.1 | 0.1 | 0.7 |
| | 300 | 13.1 | 48.9 | 4.8 | 1.4 | 0.5 | 43.0 | 0.1 | 1.3 |
| | 350 | 8.3 | 50.6 | 4.6 | 16.1 | 1.3 | 15.5 | 0.6 | 11.3 |
| | 375 | 11.3 | 40.1 | 20.7 | 3.8 | 0.6 | 8.4 | 0.3 | 26.1 |
| CAT-III | 250 | 33.5 | 34.8 | 8.3 | 3.5 | 0.9 | 44.3 | 0.7 | 7.5 |
| | 300 | 32.2 | 59.8 | 11.9 | 2.2 | trace | 20.7 | 0.9 | 4.5 |
| | 350 | 19.3 | 70.5 | 10.0 | 0.7 | 0.5 | 9.6 | trace | 8.7 |
| | 375 | 12.5 | 63.1 | 8.4 | 5.6 | 1.7 | 10 | 0.1 | 11.1 |
| CAT-IV | 250 | 35.0 | 13.7 | 1.7 | 1.8 | 0.2 | 80.5 | trace | 2.3 |
| | 300 | 23.09 | 41.7 | 9.3 | 2.6 | 0.2 | 40.9 | trace | 5.3 |
| | 350 | 21.9 | 54.2 | 8.7 | 2.3 | 0.8 | 31.6 | 0.3 | 2.1 |
| | 375 | 9.1 | 52.7 | 4.1 | 2.8 | 0.3 | 35.5 | 0.3 | 4.3 |
| CAT-V | 250 | 15.3 | 1.7 | trace | 0.1 | 0.0 | 88.3 | 0.0 | 9.9 |
| | 300 | 5.0 | 0.4 | 0.0 | 0.9 | 0.0 | 95.6 | 0.0 | 3.1 |
| | 350 | 0.8 | 4.6 | 0.0 | 15.1 | 0.0 | 58.7 | 0.0 | 21.6 |
| | 375 | 0.4 | 14.1 | 0.0 | 13.0 | 0.0 | 45.4 | 0.0 | 27.5 |

*Reaction conditions: 0.25 g catalyst, H$_2$/DMK mol ratio = 4, time-on-stream = 1 hour.

reaction low temperature, which is consistent with the exothermic nature of the direct hydrogenation of DMK.

TABLE 5

Gas-phase DMK-self condensation over n-Ru/AC/n-ZnO catalysts*

| Catalyst | $H_2$/DMK mol ratio | Conv., % | Selectivity, % | | | | | | |
|---|---|---|---|---|---|---|---|---|---|
| | | | MIBK | DIBK | MO | M | IPA | DA | Others |
| CAT-IV | 1.5 | 96.0 | 0.0 | trace | 0.0 | 0.0 | 98.7 | trace | 1.14 |
| | 3.0 | 93.9 | 0.0 | trace | 0.0 | 0.0 | 99.8 | trace | 0.17 |
| | 4.5 | 87.0 | 0.0 | trace | 0.0 | 0.0 | 99.6 | trace | 0.31 |
| | 6.0 | 35.4 | 0.0 | trace | 0.0 | 0.0 | 99.8 | trace | 0.13 |

Reaction conditions: 0.25 g catalyst, Temperature = 75° C., time-on-stream = 1 hour.

Figure 2:
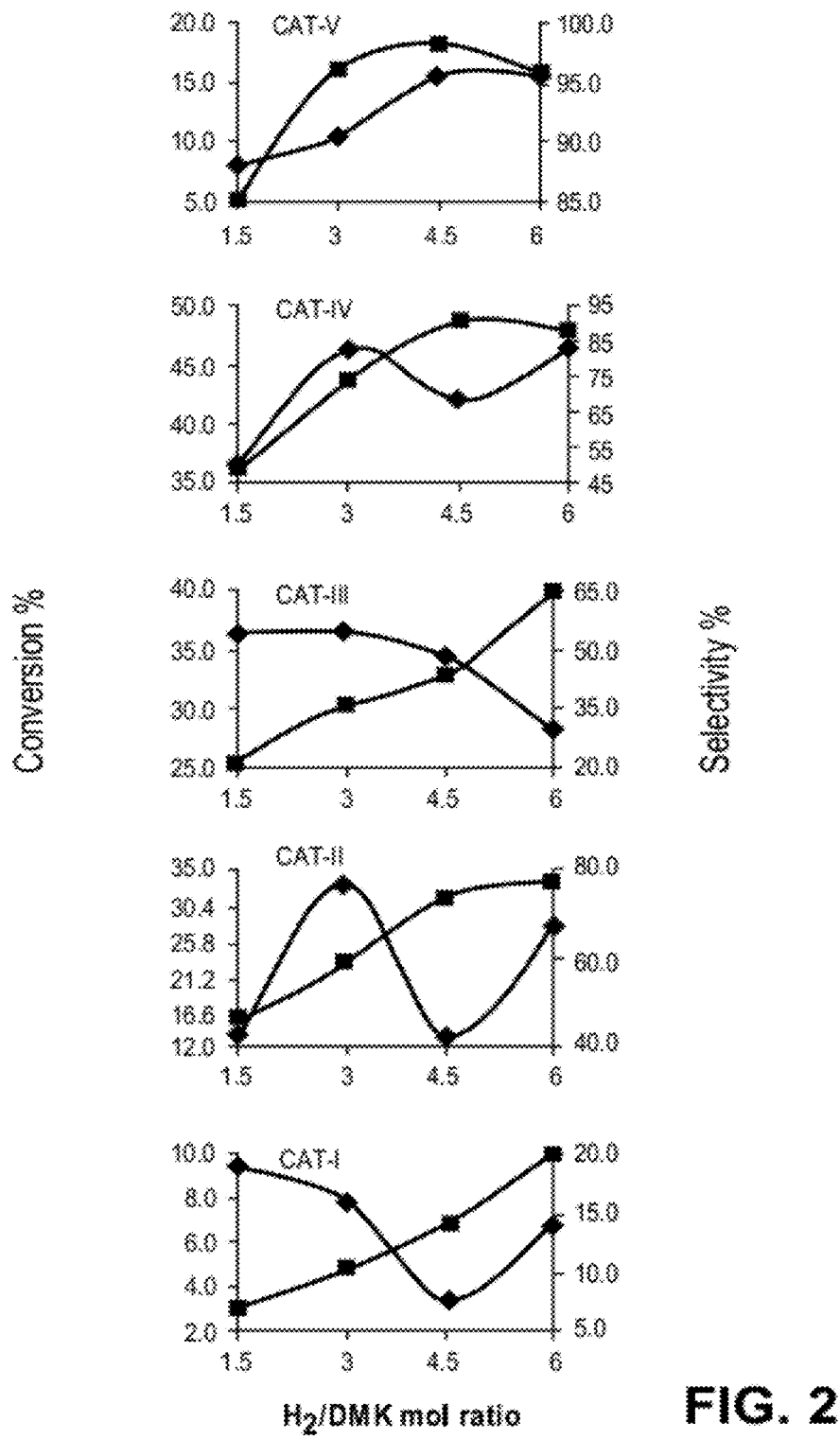
FIG. 2 shows DMK conversion and IPA selectivity vs $H_2$/DMK mol ratio for the investigated catalyst (T=250° C.: TOS=1 hr).

The variation of conversions and selectivity of the reaction at different temperatures over all the investigated catalysts (Table 1) are shown in FIG. 1. The maximum conversion and the maximum selectivity for IPA were reached at 250° C. CAT-V showed the highest selectivity towards IPA at 250° C. The selectivity towards IPA decreases upon increasing the reaction temperature for all the investigated catalysts. The condensation and dehydrogenation products catalyzed by acidic sites are favored above 250° C., while direct hydrogenation product is favored below this temperature. The effect of variation of $H_2$/DMK mol ratio on DMK conversion and IPA selectivity at 250° C. is shown in FIG. 2. This conversion increased with increasing $H_2$/DMK mol ratio up to 3 for CAT-II and CAT-III, while the maximum conversion for CAT-IV and CAT-V was attained at $H_2$/DMK mol ratio equivalent to 6. It is noticed that the selectivity towards IPA increased upon increasing $H_2$/DMK mol ratio. CAT-V showed the highest selectivity towards IPA at $H_2$/DMK ratio equal to 4.5.

The Effect of Ru-Loading

Figure 3:
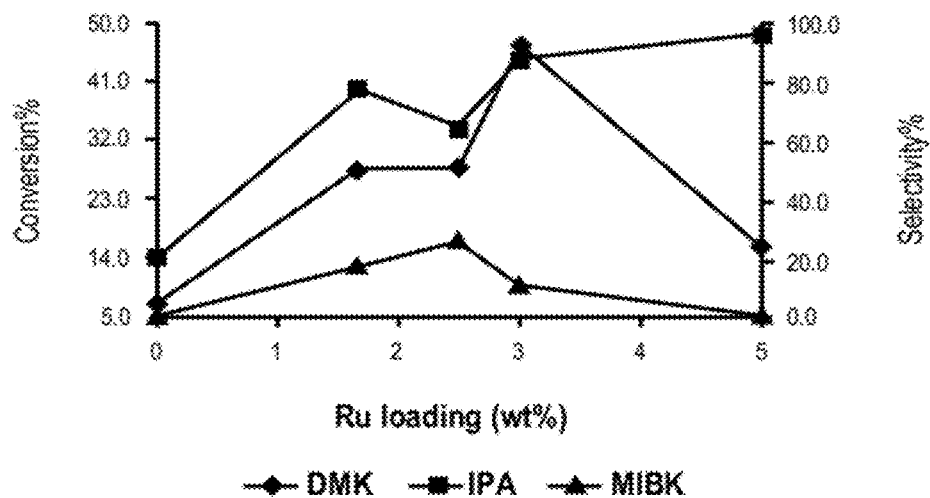
FIG. 3 shows the effect of Ru-loading on DMK conversion and product selectivity (H2/DMK mol ratio=6, temperature=250° C., TOS=1 hr).

The conversion and selectivity as a function of Ru-loading are shown in FIG. 3. DMK conversion increases with increasing Ru-loading up to 3.0 wt % and then decreases when the Ru-loading is increased to 5.0 wt %. The selectivity towards MIBK increases with increasing the Ru-loading up to 2.5 wt % and then decreases with an increased Ru-loading. The observation of the maximum MIBK selectivity at 2.5 wt % Ru-loading can be attributed to the presence of balanced multi-functional sites (hydrogenation and condensation). On the other hand, increasing of Ru-loading results in increasing in IPA selectivity except at Ru-loading of 2.5 wt %. This observation indicates that high Ru-loading favors the direct hydrogenation of DMK carbonyl group. The multifunctional composite catalyst with Ru/AC:n-ZnO equals to 1:0 (wt/wt) (CAT-V) exhibited the highest IPA selectivity. It appears that the metallic sites are very essential for the formation of IPA.

The Effect of Acidic/Basic Sites Concentration

Figure 4:
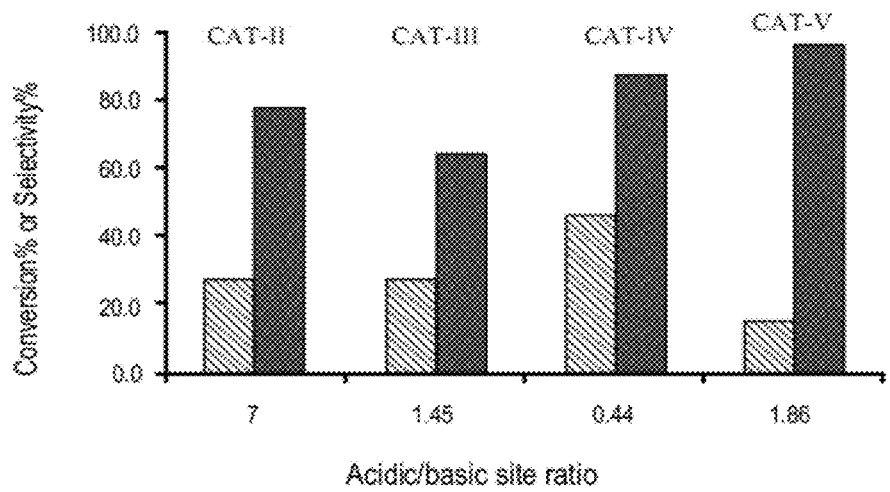
FIG. 4 shows the effect of acidic/basic site concentration ratio on DMK conversion and IPA selectivity ($H_2$/DMK mol ratio=6, temperature=250° C., TOS=1 hr).

FIG. 4 shows the comparison between CAT-II, CAT-III, CAT-IV and CAT-V in the effect of their acidic/basic sites concentration on the conversion and IPA selectivity at the best reaction conditions. CAT-IV showed the highest DMK conversion. On the other hand, CAT-V showed the highest selectivity towards IPA, but with a much lower conversion rate. These results show that higher activity, more direct hydrogenation products were obtained over relatively highly acidic catalyst.

The foregoing examples have been provided for the purpose of explanation and should not be construed as limiting the present disclosure. While the present disclosure has been described with reference to an exemplary embodiment, changes may be made within the perview of the appended claims, without departing from the scope and spirit of the present disclosure in its aspects. Also, although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the instant claims. Accordingly, the specification and drawings are to be regarded in an illustrative rather than in a restrictive sense.

What is claimed is:

1. A method of making a composite catalyst, comprising:
   reacting a zinc sulphate, sodium pyruvate, hydroxyl amine hydrochloride and sodium biocarbonate to make a zinc pyruvic acid oxime;
   performing a thermal pyrolysis of the zinc pyruvic acid oxime to produce n-ZnO; mechanical mixing of a ruthenium supported on activated charcoal and the n-ZnO at a specific weight ratio; and
   grinding the ruthenium supported on activated charcoal and the n-ZnO having a certain ratio to form a composite catalyst to be used for making an isopropyl alcohol from a dimethyl ketone and hydrogen in gas phase.

2. The method of making the composite catalyst as in claim 1, wherein the ratio of the ruthenium supported on activated charcoal and the n-ZnO is between 0:1 to 3:2 and 1:0.

3. The method of making the composite catalyst, wherein the composite catalyst is ruthenium nano-particle-supported on activated charcoal/nano-zinc oxide.

4. A method of using a composite catalyst, comprising:
   reacting a zinc sulphate, sodium pyruvate, hydroxyl amine hydrochloride and sodium biocarbonate to make a zinc pyruvic acid oxime;
   performing a thermal pyrolysis of the zinc pyruvic acid oxime to produce n-ZnO;
   mechanically mixing a ruthenium supported on activated charcoal and the n-ZnO in a certain ratio; and
   grinding the ruthenium supported on activated charcoal and the n-ZnO having the certain ratio to form a composite catalyst; and
   reacting dimethyl ketone, hydrogen and the composite catalyst having the certain ratio to form isopropyl alcohol.

5. The method of using a composite catalyst as in claim 4, wherein the composite catalyst is ruthenium nano-particle-supported on activated charcoal/nano-zinc oxide.

6. The method of using a composite catalyst as in claim 4, wherein the ratio of the ruthenium supported on activated charcoal and the n-ZnO is between 0:1 to 3:2 and 1:0.

7. The method of using a composite catalyst as in claim 4, further comprising:
   mixing dimethyl ketone and hydrogen in a molar ratio before reacting with the composite catalyst.

8. The method of using a composite catalyst as in claim 7, wherein the molar ratio is between 4 to 6.

9. The method of using a composite catalyst as in claim 4, further comprising:
reacting the dimethyl ketone, hydrogen and the composite catalyst in a temperature that is optimal to a specific composite catalyst.

10. The method of using a composite catalyst as in claim 9, wherein the optimal temperature is between 75-375° C.

11. The method of using a composite catalyst as in claim 10, wherein the optimal temperature is between 75-200° C.

12. The method of using a composite catalyst as in claim 9, wherein the specific composite catalyst is CAT-I, CAT-II, CAT-III, CAT-IV AND CAT-V.

13. The method of using a composite catalyst as in claim 9, wherein the specific composite catalyst is CAT-IV.

* * * * *